United States Patent
Komatsu et al.

(10) Patent No.: US 9,867,968 B2
(45) Date of Patent: Jan. 16, 2018

(54) BALLOON TUBE, BALLOON, BALLOON CATHETER, AND BALLOON TUBE FABRICATION METHOD

(71) Applicant: KANEKA CORPORATION, Osaka-shi, Osaka (JP)

(72) Inventors: Toshiyuki Komatsu, Settsu (JP); Takuro Koda, Settsu (JP)

(73) Assignee: KANEKA CORPORATION, Osaka-Shi (JP)

( * ) Notice: Subject to any disclaimer, the term of this patent is extended or adjusted under 35 U.S.C. 154(b) by 608 days.

(21) Appl. No.: 14/373,763

(22) PCT Filed: Feb. 7, 2013

(86) PCT No.: PCT/JP2013/052828
§ 371 (c)(1),
(2) Date: Jul. 22, 2014

(87) PCT Pub. No.: WO2013/118807
PCT Pub. Date: Aug. 15, 2013

(65) Prior Publication Data
US 2015/0018866 A1    Jan. 15, 2015

(30) Foreign Application Priority Data

Feb. 9, 2012   (JP) ................. 2012-026490

(51) Int. Cl.
*A61M 29/00*    (2006.01)
*A61M 25/10*    (2013.01)
(Continued)

(52) U.S. Cl.
CPC ...... *A61M 25/104* (2013.01); *A61M 25/1002* (2013.01); *A61M 25/1029* (2013.01);
(Continued)

(58) Field of Classification Search
CPC ............ A61M 25/104; A61M 25/1002; A61M 25/1029; A61M 25/1027; A61M 2025/1059; B29C 49/08; B29C 55/26
See application file for complete search history.

(56) References Cited

U.S. PATENT DOCUMENTS

| 4,820,349 A * | 4/1989 | Saab ................. A61M 25/1029 604/913 |
| 5,470,313 A * | 11/1995 | Crocker ............ A61M 25/1002 604/103.07 |

(Continued)

FOREIGN PATENT DOCUMENTS

| JP | 8-38609 A | 2/1996 |
| JP | 2008-23270 A | 2/2008 |
| JP | 2010-201007 A | 9/2010 |

OTHER PUBLICATIONS

International Search Report, issued in PCT/JP2013/052828, dated Apr. 16, 2013.

*Primary Examiner* — Ashley Fishback
(74) *Attorney, Agent, or Firm* — Birch, Stewart, Kolasch & Birch, LLP

(57) ABSTRACT

In a balloon tube (10) which is processed after it is mounted on a mold, a bag part (14) has a plurality of parts having a different drawability in a radial direction centered around an axial direction X, disposed along the axial direction X. The highest drawability part (11), which has the highest drawability, is disposed to separate from both ends of the bag part (14) in the axial direction X thereof. The balloon tube (10) is preferable to stably fabricate a balloon having a uniform film thickness.

4 Claims, 5 Drawing Sheets

(51) Int. Cl.
*B29C 49/08* (2006.01)
*B29C 55/26* (2006.01)
*B29K 101/12* (2006.01)
*B29K 105/00* (2006.01)
*B29L 31/00* (2006.01)

(52) U.S. Cl.
CPC .............. *B29C 49/08* (2013.01); *B29C 55/26* (2013.01); *A61M 2025/1059* (2013.01); *A61M 2025/1081* (2013.01); *A61M 2025/1086* (2013.01); *B29K 2101/12* (2013.01); *B29K 2105/253* (2013.01); *B29L 2031/7543* (2013.01); *F04C 2270/041* (2013.01)

(56) References Cited

U.S. PATENT DOCUMENTS

| | | | |
|---|---|---|---|
| 2003/0028210 A1* | 2/2003 | Boyle | A61F 2/82 606/192 |
| 2005/0043679 A1* | 2/2005 | Devens, Jr. | A61M 25/1002 604/103.06 |
| 2005/0228428 A1* | 10/2005 | Ali | A61M 25/1027 606/194 |

* cited by examiner

[Fig. 1]
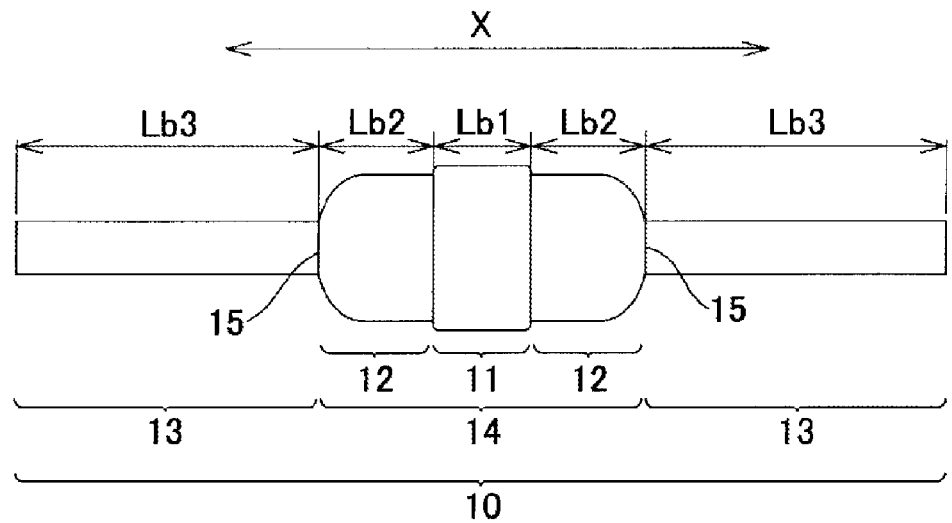
[Fig. 2]
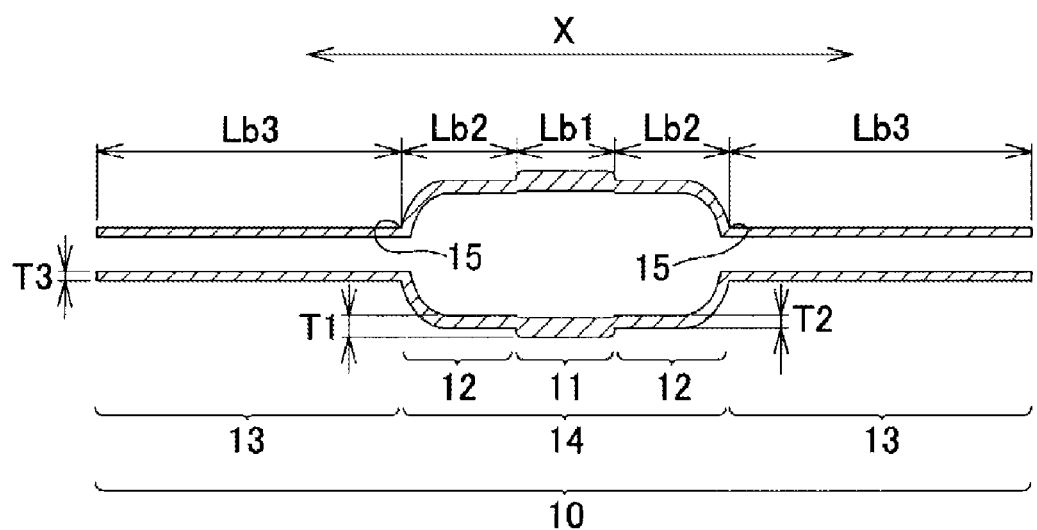

[Fig. 3]
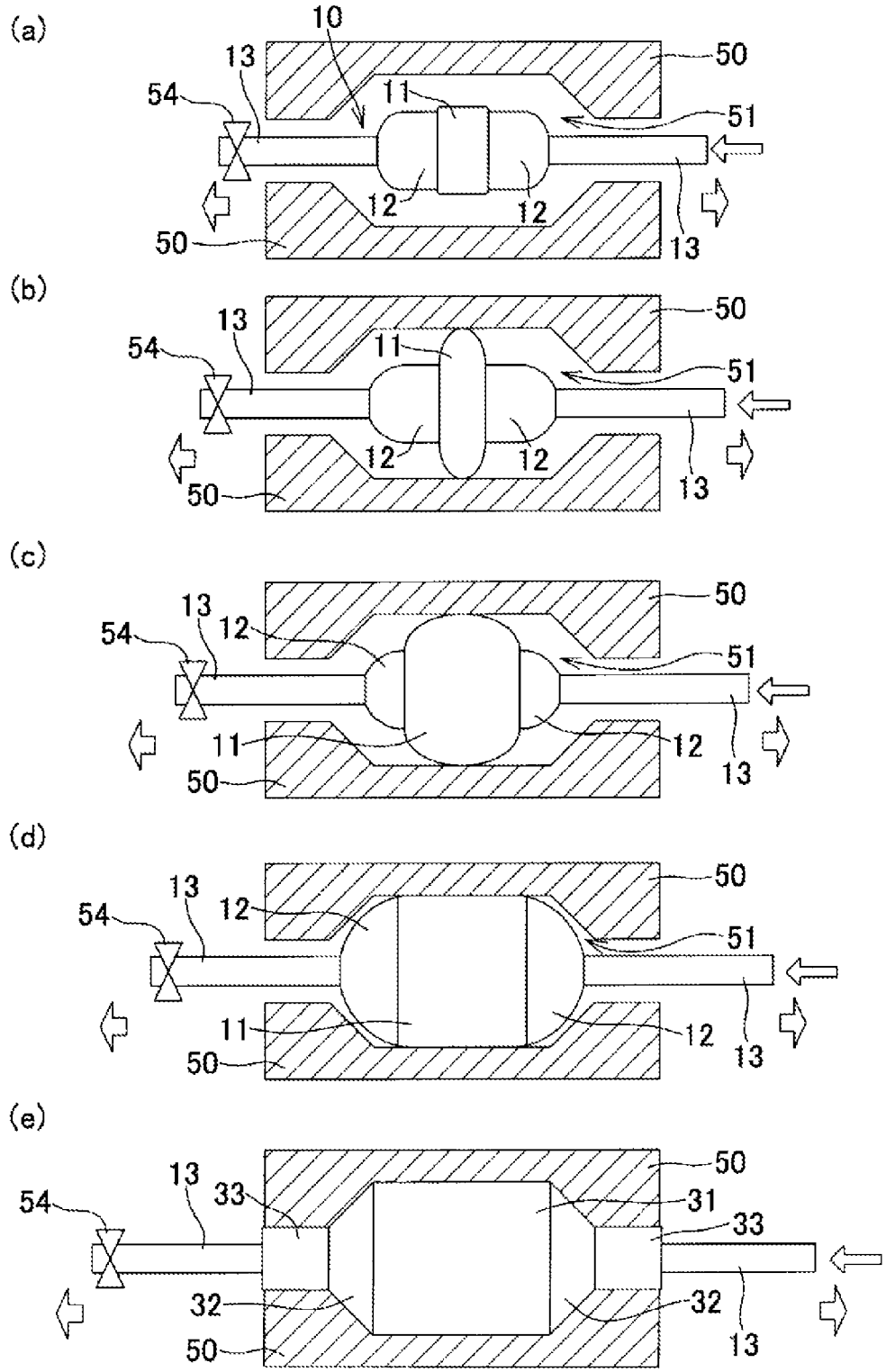

[Fig. 4]
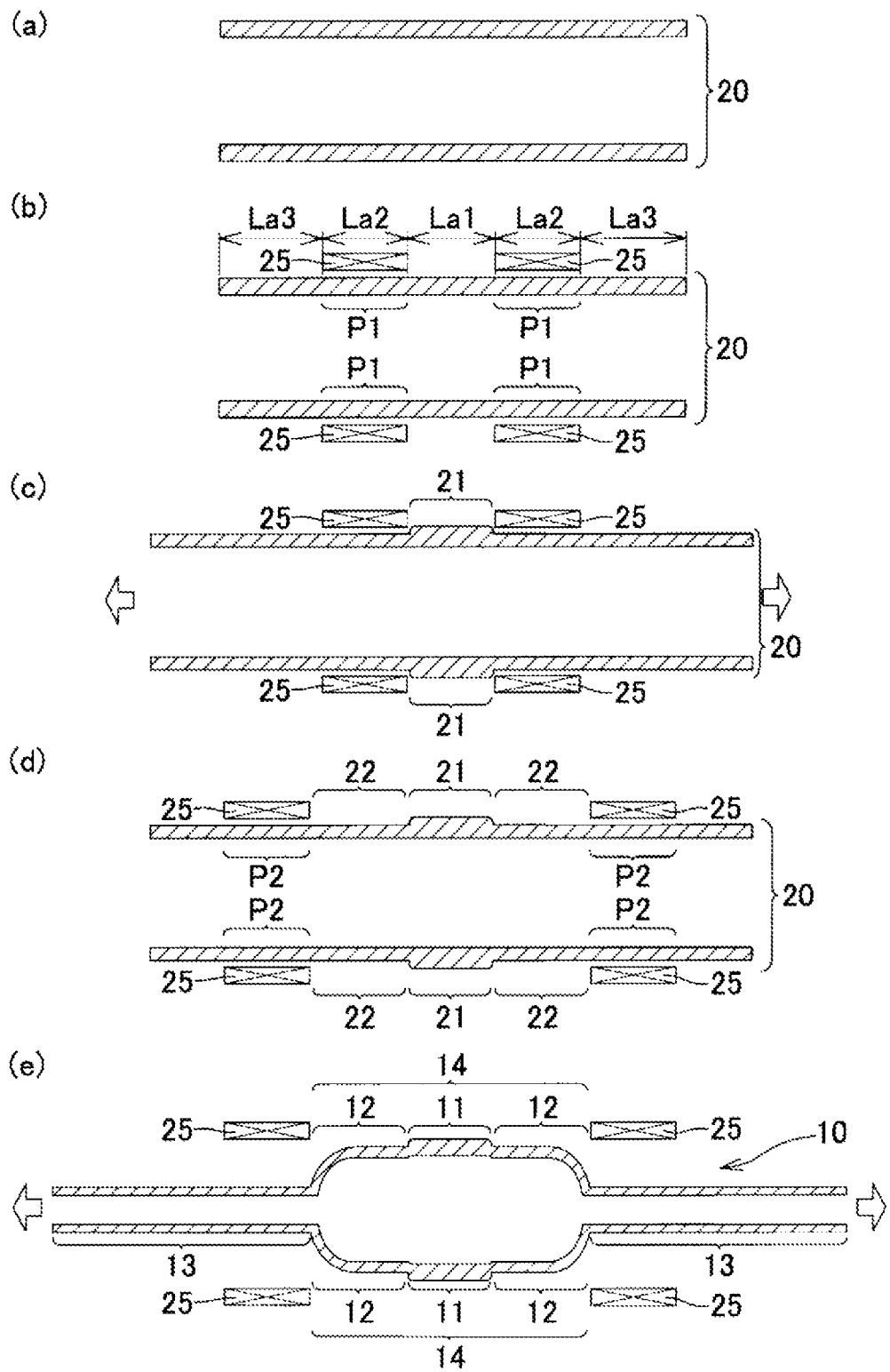

[Fig. 5]
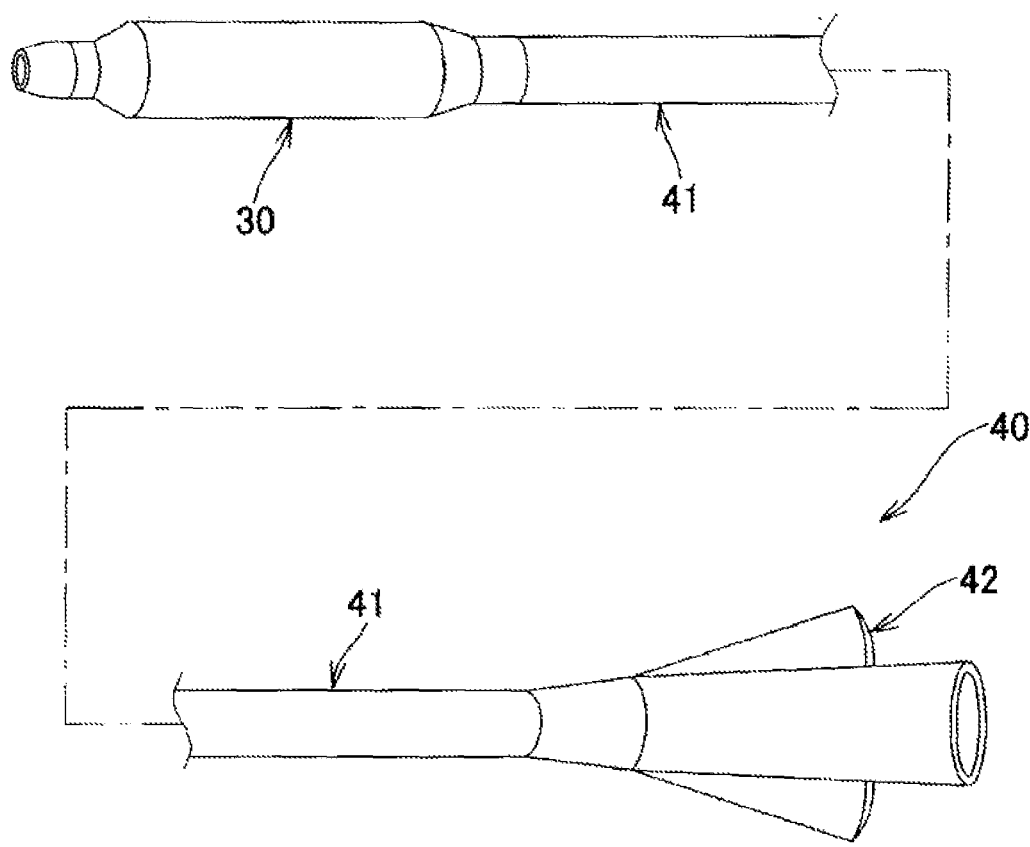
[Fig. 6]
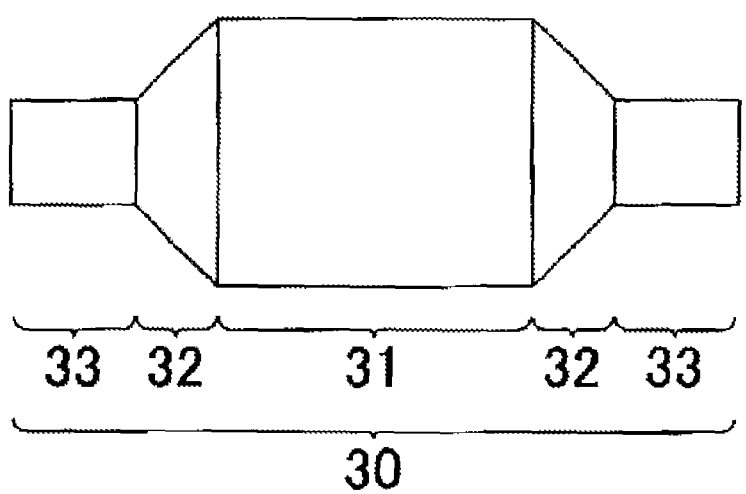

[Fig. 7]
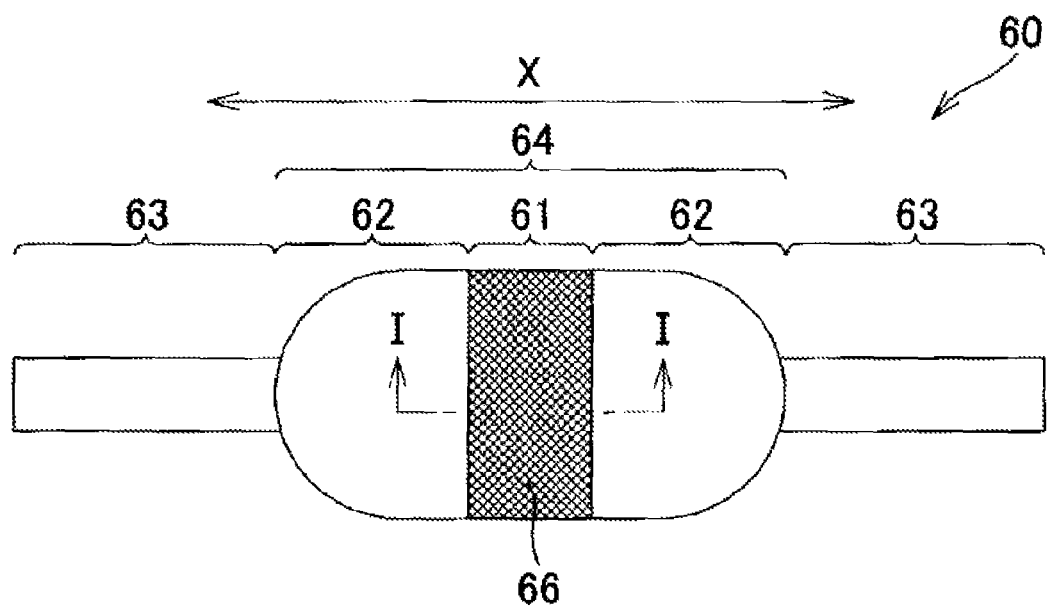
[Fig. 8]
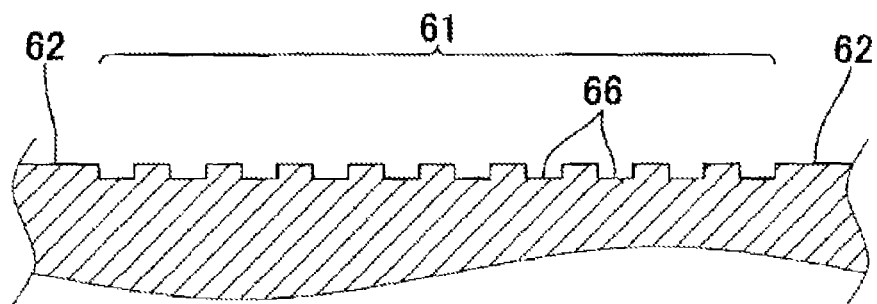

BALLOON TUBE, BALLOON, BALLOON CATHETER, AND BALLOON TUBE FABRICATION METHOD

TECHNICAL FIELD

The present invention relates to a balloon tube, a balloon, a balloon catheter, and a balloon tube fabrication method.

BACKGROUND ART

Percutaneous angioplasty such as PTA (Percutaneous Transluminal Angioplasty) or PTCA (Percutaneous Transluminal Coronary Angioplasty) is a therapy in which a narrow part or an occluded part generated in a vascular lumen is removed, and a procedure for recovering or improving blood flow in a coronary artery or a peripheral blood vessel.

In such a percutaneous angioplasty, catheters formed of a medical tube are used. In usual, the catheter is advanced while a route (blood vessel) is selected, until it reached a narrow part to be treated. In addition, for example, in a case of a balloon catheter, after the catheter reaches a part to be treated, a pointed end of the catheter passes through a narrow part and a balloon, which is disposed around the pointed end, dilates the narrow part.

This balloon has desirably a physical property in which it is easily folded to a small diameter in order to improve pass characteristic until a narrow part to be treated, and for this end, a thinner film thickness is better. On the other hand, however, it is necessary that the pressure resistance of the balloon is enhanced by providing a uniform and above certain film thickness to the balloon, in order to improve an expansive force of the balloon at the narrow part. In order to make the diameter smaller, it is preferable that the film thickness of the balloon is thinner, however, a balloon having a partially extremely thin (that is, ununiform) film thickness, because of excessive pursuit of thinness, has a deteriorated pressure resistance.

It is desirable, accordingly, that the film thickness of the balloon is made as thinner as possible while the uniformity is kept. For this end, for example, Patent Document 1 discloses a blow-molding method in which a tube, which has been drawn in an axial direction while a balloon part is left, is mounted on a balloon metal mold when a balloon tube is formed.

CITATION LIST

Patent Literature

Patent Document 1: JP-A No. 2008-23270

SUMMARY OF INVENTION

Technical Problem

The method of Patent Document 1, however, does not consider a temperature distribution in a metal mold used in the blow-molding. As a result, if the temperature distribution of the metal mold deviates from a desired temperature distribution, the balloon tube is expanded in an unwanted way (for example, a starting point of the drawing in the balloon tube deviates from a desired position when blow-molding is performed), and thus, it is difficult to form a balloon having a uniform film thickness.

The present invention has been made in order to solve the problems described above. The object of the invention is to provide a balloon tube, or the like, which is preferable for stably fabricating a balloon having a uniform film thickness.

Solution to Problem

The balloon tube is processed after it is mounted on a mold. Such a balloon tube includes a bag part. On the bag part, a plurality of parts having a different drawability in a radial direction is disposed in an axial direction of the balloon tube. Among them, the highest drawability part, which is a part having the highest drawability is disposed to separate from both ends of the bag part in the axial direction of the balloon tube.

The highest drawability part preferably has the thickest film thickness in the bag part.

It is also desirable that a sleeve formed from a film having a film thickness thinner than the film thickness of the bag part is disposed adjacent to at least one side of the bag part in the axial direction of the balloon tube.

It is also desirable that the highest drawability part has a cut in its surface.

It is also desirable that the highest drawability part is subjected to a chemical processing for increasing the drawability.

Both of a balloon fabricated from the balloon tube described above and a balloon catheter including such a balloon can be also the present invention.

A fabrication method of a balloon tube which is processed after it is mounted on a mold, including the following steps of a first heating step in which two first parts which are separated from each other in an axial direction of a tube material, which is a base of the balloon tube; a first drawing step in which at least one end of the tube material is drawn to form the highest drawability part at which the drawability is the highest between the two first parts; a second heating step in which, in the tube material, two second parts, which are separated from each other so that all of the plurality of the heated positions of the first parts are sandwiched between them, are heated; and a second drawing step in which at least one end of the tube material is drawn to form a bag part having the highest drawability part disposed between the two second parts.

In the fabrication method of a balloon tube, it is desirable in the second drawing step to form sleeves adjacent to both sides of the bag part.

It is also desirable that the fabrication method of a balloon tube satisfies the following formula (1):

$$(Lb1/La1) < (Lb2/La2) < (Lb3/La3) \quad \text{Formula (1)}$$

wherein $La1$: the shortest distance between the first parts in the tube material before the first heating step;

$La2$: a full length of one of the first parts in the axial direction of the tube material before the first heating step;

$La3$: the shortest distance from one end of the tube material to the first part;

$Lb1$: a full length of the highest drawability part in the axial direction of the balloon tube after the second drawing step;

$Lb2$: the shortest distance from one end of the bag part to the highest drawability part in the axial direction of the balloon tube after the second drawing step; and Lb3: a full length of the sleeve adjacent to one side of the bag part after the second drawing step.

Advantageous Effects of Invention

According to the balloon tube of the present invention, a balloon having a uniform film thickness can be stably fabricated.

BRIEF DESCRIPTION OF THE DRAWINGS

FIG. 1 is a side view showing one embodiment of a balloon tube.

FIG. 2 is a cross-sectional view showing one embodiment of a balloon tube.

FIG. 3 is an explanatory drawing showing fabrication steps of a balloon.

FIG. 4 is an explanatory drawing showing fabrication steps of a balloon tube.

FIG. 5 is a perspective view showing a balloon catheter.

FIG. 6 is a side view showing a balloon.

FIG. 7 is a side view showing another embodiment of a balloon tube.

FIG. 8 is a partially enlarged cross-sectional view of the balloon tube shown in FIG. 7 in an I-I direction.

DESCRIPTION OF EMBODIMENTS

One embodiment is explained based on the drawings as below. In the drawings, signs for members may sometimes be omitted as a matter of convenience, and in such a case, please see other drawings. In addition, sizes of various members in the drawing are adjusted so as to ease to read as a matter of convenience.

FIG. 5 is a perspective view showing a balloon catheter 40, which is one kind of the catheters; and FIG. 6 is a side view showing a balloon 30 taking up from the balloon catheter 40.

As shown in FIG. 5, on the balloon catheter 40, the balloon 30 is disposed at one end of a catheter shaft 41, and, on the other hand, a hub 42 is disposed at the other end of the catheter shaft 41.

The balloon 30 dilates a blood vessel, which is blocked due to stenotic lesion (such as a thrombus), to secure blood flow. Such a balloon 30 is a tubular member (a hollow member), and is disposed at one side of the balloon catheter 40.

A tubular part having a smaller diameter than a diameter at around the center of both ends of the balloon 30, as shown in FIG. 6, is hereinafter referred to as a capillary part 33. A tubular part around the center of the balloon 30 is referred to as a main tube part 31. A tubular part which is between the main tube part 31 and the capillary part 33, and is tapered off toward the both ends of the balloon 30 is referred to as a taper part 32.

In the balloon catheter 40, a side where the balloon 30 is disposed is referred to as a distal side and a side opposite to the distal side is referred to as a proximal side. When a side in each member is specified, it may sometimes be referred to as a distal side or a proximal side. In each member, the end of the distal side is referred to as a distal end and a part in the vicinity of the distal end is referred to as a distal end part; and the end of the proximal side is referred to as a proximal end and a part in the vicinity of the proximal end is referred to as a proximal end part.

Here, the balloon 30 is explained in detailed. The balloon 30 is preferably fabricated by blow-molding (for example, biaxially drawing blow-molding) a balloon tube 10, as shown in, for example, FIG. 1 which is the side view and FIG. 2 which is the cross-sectional view, in a state in which it is housed in an interior space (a cavity) of a metal mold [a mold] for balloon-molding.

The balloon tube 10 is a hollow member (a tubular member) and includes a bag part 14. Sleeves 13, which are hollow members, are connected to both sides of the bag part 14 (a hollow part in the bag part 14 and a hollow part of the sleeve 13 flow through each other).

On the bag part 14, a plurality of parts is disposed along an axial direction X of the balloon tube 10. More specifically, on the bag part 14, a plurality of parts having a different drawability in a radial direction centered around an axial direction X, are disposed along the axial direction X.

In the present application, the "drawability in the radial direction" shows a level of easiness of drawing in the radial direction of the balloon tube 10 upon the blow-molding, and means, for example, that a part having a high drawability is more easily drawn (more easily blown) in the radial direction than a part having a low drawability, in a constant blowing pressure. When the balloon tube 10 is drawn in the radial direction, a drawing direction of a film forming the balloon tube 10 can be defined by an axial direction X and a circumferential direction of the balloon tube 10.

In the case of the balloon tube 10 shown in FIG. 1 and FIG. 2, the highest drawability part 11, which is a part having the highest drawability, is disposed to separate from both ends 15 and 15 of the bag part 14 (both ends of the bag part 14 in the axial direction X). More specifically, the highest drawability part 11 is disposed in a middle of the balloon tube 10, and side end parts 12 [a part of the bag part 14 excluding the highest drawability part 11] are disposed adjacent to the both sides of the highest drawability part 11 (the side end parts 12 and 12 have a drawability in the radial direction lower than that of the highest drawability part 11).

The difference in the drawability between the highest drawability part 11 and the side end part 12 is based on the difference in the film thickness (wall thickness) of the parts 11 and 12 in the example of this drawing. More specifically, as shown in FIG. 2, the film thickness T1 of the highest drawability part 11 is thicker than the film thickness T2 of the side end part 12. The film thickness T2 of the side end part 12 is thicker than the film thickness T3 of the sleeve 13 (i.e., a relationship of T1>T2>T3 is satisfied).

Specific examples of the numerical value may include as follows:

0.19 mm≤T1≤0.25 mm
0.11 mm≤T2≤0.18 mm
0.06 mm≤T3≤0.10 mm

In the case of such a balloon tube 10, more specifically the balloon tube 10 including a bag part 14 having the highest drawability part 11 and the side end parts 12 and 12 disposed on the both sides of the highest drawability part, blow-molding is performed as shown in FIG. 3A to FIG. 3E to provide a balloon 30.

As shown in FIG. 3A, first, the balloon tube 10 is put in a metal mold 50 having a cavity 51, and then one end of one of the sleeves 13 included in the balloon tube 10 is sealed with a clip 54 (for example, one end of the sleeve 13, exposing from the metal mold 50, is sealed with the clip 54). During the steps shown in FIGS. 3A to 3E, the metal mold 50 is heated at a desired temperature.

After that, from an opening of the other sleeve 13 included in the balloon tube 10, fluid such as gas is injected thereto (see a black arrow), and at the same time, the balloon tube 10 is drawn (for example, it is drawn so as to separate the two sleeves 13 and 13 from each other; see a white arrow).

At that time, first, the highest drawability part 11 is expanded while it is elongated in the radial direction by the injection of the fluid. When the expansion is further advanced, the highest drawability part 11 is brought into contact with an inner wall of the metal mold 50, as shown in FIG. 3B, to regulate the drawing in the radial direction (i.e., the highest drawability part 11 in the balloon tube 10 does not become larger than the cavity 51).

The injection of the fluid to the balloon tube 10 is, however, still continued after that and thus the highest drawability part 11 is expanded while it is elongated in the axial direction X, as shown in FIG. 3C. More specifically, the highest drawability part 11 is elongated from the vicinity of the center to the side end parts 12 and 12, and at the same time the elongated parts is elongated in the radial direction, thus resulting in that the highest drawability part 11 is elongated in the axial direction X and expanded in the radial direction.

By the further continued injection of the fluid into the balloon tube 10, the side end parts 12 and 12 disposed adjacent to the highest drawability part 11 are also elongated in the axial direction X and are expanded in the radial direction, as shown in FIG. 3D (the side end parts 12 of the balloon tube 10, of course, do not become larger than the cavity 51, as in the case of the highest drawability part 11).

When the injection of the fluid into the balloon tube 10 is continued, the balloon tube 10 is expanded along the shape of the cavity 51, as shown in FIG. 3E. After the balloon tube 10 is formed into a balloon 30 having a desired shape, the metal mold 50 is cooled. After that, unnecessary parts of the sleeve 13 are cut off, and the balloon 30 which is attached to a catheter shaft 41 as shown in FIG. 6 is completed.

As described above, when the highest drawability part 11, which has the highest drawability in the radial direction, is disposed at the middle of the balloon tube 10, more specifically at the middle of the bag part 14 of the balloon tube 10, regardless of the temperature distribution variation in the axial direction of the metal mold 50 or the position of the balloon tube 10 in the axial direction of the metal mold 50, the drawing starts from the highest drawability part 11 as shown in FIG. 3B.

This suppresses the quality change of the balloon 30 (formation of the ununiform film thickness), caused by varying the starting position of the drawing of the balloon tube 10 per balloon 30 in the blow-molding using the metal mold 50. From the balloon tube 10 having the highest drawability part 11, accordingly, the high quality balloon 30 having a uniform film thickness can be stably fabricated.

In addition, when such a balloon tube 10 is used, high quality balloon 30 is stably fabricated, without excessive need of an advanced operation on the fabrication, for example, an improvement of the precision of the metal mold, a suppression of disturbance caused by an outdoor temperature, or a suppression of variation in resin materials.

According to the method described above, because the vicinity of the center of the balloon tube 10 serves as the starting point of the drawing when the blow-molding is performed, the bag part 14 is disposed at the vicinity of the center of the balloon tube 10, and there is difference in the film thickness between the highest drawability part 11 and the side end part 12 of the bag part 14. The present invention, however, is not limited thereto.

For example, the highest drawability part of the balloon tube may be subjected to a chemical processing for increasing the drawability, or cuts may be formed into the surface of the highest drawability part. The chemical processing may include, for example, a processing for adjusting a molecular orientation in an axial direction of a resin forming the balloon tube, or a processing for changing properties of a resin forming the balloon tube such as coating a chemical agent capable of changing the drawability of a resin. The case in which the highest drawability part is subjected to the chemical processing for increasing the drawability includes a case in which both of the side end parts of the highest drawability part is subjected to a chemical processing for decreasing the drawability, regardless of whether or not the highest drawability part is subjected to the chemical processing.

The "cut" formed into the surface of the highest drawability part may include, for example, depressions having a fine width formed into the surface of the highest drawability part. The structure of the depression can be appropriately decided, considering the drawability.

Examples of the chemical processing for increasing the drawability of the highest drawability part of the balloon tube may include, for example, a processing of adjusting a molecular orientation in an axial direction of a resin forming the balloon tube.

The adjustment of the degree of molecular orientation in the axial direction of the resin forming the balloon tube 10 controls so that the vicinity of the center of the balloon tube 10 serves as the starting point of the drawing when the blow-molding is performed.

In the adjustment of the degree of molecular orientation, annealing, for example, is used. More specifically, the balloon tube 10, i.e., the sleeves 13 in the balloon tube 10 and the vicinity of the center and other parts in the bag part 14 (a part of the bag part 14 adjacent to the sleeves 13), formed by an extrusion molding, have a molecular orientation drawn in an axial direction. When each part is appropriately heated, however, the molecular orientation in the axial direction is relaxed and the drawability of a desired part is increased. For example, in a balloon tube 10 having the same molecular orientation in the axial direction, when the vicinity of the center of the bag part 14, which part will become the highest drawability part, is heated at a predetermined temperature, the degree of molecular orientation at the part is relaxed to increase the drawability upon the balloon forming. In a case where crystallization is advanced by cooling after the degree of orientation is relaxed by heating, a balloon is formed before cooling. On the other hand, it is also possible to increase the drawability of the part which will become the highest drawability part by heating and cooling parts other than the vicinity of the center of the bag part 14, which will become the highest drawability part, to advance the crystallization of the parts thereby reducing the drawability of the parts. (For convenience, the explanations have been made using the same signs as used in FIGS. 1 and 2 showing the example in which there is the difference in the film thickness, but when the degree of molecular orientation is adjusted, it is not necessary that there is a difference in the film thickness between the highest drawability part and the side end part of the bag part. The same applies to examples described below.)

As described above, the annealing can control so that the vicinity of the center of the balloon tube 10 serves as the starting point of the drawing in the fabrication of the balloon 30 by blow-molding (The drawing amount of each part in the balloon tube 10 may be changed by means other than the annealing).

In order to make the vicinity of the center of the balloon tube 10 to serve as the starting point of the blowing, coating with a solvent for increasing the drawability (such as alcohols) may be performed before the blow-molding to soften the resin at the vicinity of the center of the bag part 14, or, conversely, coating with a solvent for decreasing the drawability may be performed to make a resin at parts other than the vicinity of the center of the bag part 14 difficult to be drawn.

In examples in which cuts are formed into the surface of the highest drawability part, the structure in which depressions having a fine width are formed into the surface may include, for example, a fine groove formed into the surface of the highest drawability part by leaser light and the like. It is needless to say that the processing into grooves by the laser light is a fine groove which does not affect the pressure resistance of the balloon 30. The structure of the fine groove may include single or multiple linear grooves in parallel to an axial direction, single or multiple grooves continued linearly in a circumferential direction, grooves in the combination of the two structures described above, and the like. The grooves of the combination of the two structures may include latticed grooves which are intersected with a right angle or an angle other than the right angle. When the multiple grooves are formed, a distance or pitch between the grooves may be appropriately designed considering the drawability. The depth of the groove is not particularly limited, so long as the pressure resistance of the balloon 30 is not affected, as described above. For example, when the highest drawability part of the balloon tube has a film thickness of 100 to 600 μm and an outer diameter of 0.4 to 2.5 mm, the depth may be from 0.8 to 1.6 μm. The width of the groove is not particularly limited, so long as the drawability and the uniformity of the balloon film thickness are not affected. For example, when the highest drawability part of the balloon tube has a film thickness of 100 to 600 μm, and an outer diameter of 0.4 to 2.5 mm, the maximum width may be from 0 to 3 μm. The maximum width of 0 μm refers to a state in which the groove is brought into contact with both wall parts.

It is not necessary to be clear that the drawability is improved by forming the cuts, as described above, but it can be considered that the phenomenon is caused by increasing the surface area by cutting the surface.

FIG. 7 is a side view schematically showing a balloon tube 60 having the highest drawability part 61 into which cuts are formed into the surface of the middle part of the bag part 64; and FIG. 8 is a partially enlarged cross-sectional view of FIG. 7 in an I-I direction. The balloon tube 60 shown in FIGS. 7 and 8 is a hollow member (a tubular member) and includes a bag part 64. In addition, sleeves 63, which are hollow members, are connected to both sides of this bag part 14 (a hollow part in the bag part 64 and a hollow part of the sleeve 63 flow through each other). In the bag part 64, side end parts 62 are disposed adjacent to both sides of the highest drawability part 61 along the axial direction X of the balloon tube 60. The film thickness of the bag part 64 is made thicker than the film thickness of the sleeve 63. Into the surface of the highest drawability part 61, latticed grooves 66, which are formed of multiple straight lines intersecting perpendicularly to each other, are formed. Two straight lines (diagonal lines), which is formed by connecting opposed apexes of each quadrate forming the lattice, are lines in a direction parallel to the axial direction X of the balloon tube 60 and lines in a direction perpendicular to the axial direction X.

The resin forming the balloon tube 10 (60) is not particularly limited. Examples thereof may include polyolefins such as polyethylene and polypropylene, polyamide, polyurethane, polyester, polyolefin elastomers, polyamide elastomers, polyurethane elastomers, polyester elastomers, and the like. They may be used alone or multiple resins thereof may be used. Of these resins, the polyamide elastomer is particularly preferable, because it has a high pressure resistance and flexibility capable of realizing good blood vessel pass characteristic.

The balloon tube 10 is fabricated based on a tube material 20. For example, the balloon tube 10 is fabricated through steps as shown in FIG. 4A to FIG. 4E. Here, the tube material refers to a material having a cylindrical structure. Of the tube materials, a cylinder having an outer diameter and an inner diameter, which are constant in the axial direction, is preferable. The example shown in FIG. 4 shows an example in which a balloon tube having the structure shown in FIGS. 1 and 2 is fabricated. There may be a case in which holding parts are provided at both ends of the tube material 20 in order to draw the tube material 20, but they are omitted in the drawings and explanations described below.

As shown in FIG. 4A, the tube material 20 is first prepared. Then, as shown in FIG. 4B, first parts P1 and P1, which are separated from each other, are heated in the tube material 20 [a first heating step]. The first part P1 is, for example, a circumference part (a ring part) in the tube material 20. The heating is performed, for example, by using a heater 25. The heating temperature is preferably a temperature higher than a glass transition temperature of a resin forming the tubular material.

Subsequently, for example as shown in FIG. 4C, the both ends of the tube material 20 are drawn [a first drawing step]. When the tube material 20 is drawn as described above (see white arrows), the first parts P1 and P1, which are heated, and parts from the first parts P1 and P1 to the both ends of the tube material 20 are elongated, while the film thickness of a part between P1 and P1 is almost maintained. At that time, the film thickness of the elongated parts is thinner than the film thickness of the part 21 between the first parts P1 and P1. The part shown by the sign 21 will become the highest drawability part. The material may be drawn while it is heated. For example, it could be considered that when a width (La2) of the first part P1 is larger than the heater 25, in order to maintain the heating state, the material is drawn with heating while the heater 25 is moved.

Further, as shown in FIG. 4D, in the tube material 20, two second parts P2 and P2, which are separated from each other so that the all heated positions of the first parts P1 and P1 (for example, the two positions of the heaters 25 in FIG. 4C) are sandwiched between them, are heated [a second heating step]. (The second part P2 is a circumference part of the tube material 20, as the first part P1, and the like. The heating is performed, for example, by using the heater 25). The heating temperature is preferably a temperature higher than a glass transition temperature of a resin forming the tubular material.

Further, as shown in FIG. 4E, the both ends of the tube material 20 are drawn [a second drawing step]. When the tube material 20 is drawn as described above, the second parts P2 and P2, which are heated, and parts from the second parts P2 and P2 to the both ends of the tube material 20 are elongated, while the film thickness of a part between P2 and P2 is almost maintained. At that time, the film thickness of the elongated parts is thinner than the film thickness of the parts between the second parts P2 and P2 (in particular, the parts shown by the sign 22 on the both sides of the part shown by the sign 21). As a result, the part 21, which will become the highest drawability part, is turned to the highest drawability part 11, and the parts shown by the sign 22 on the both ends of the part 21, which will become the highest drawability part, are turned to the side end parts 12, whereby the bag part 14 formed of the highest drawability part 11 and the side end parts 12 and 12 are formed. In addition, sleeves 13 and 13 are formed on the both ends of the bag part 14, and finally the balloon tube 10 as shown in FIG. 2 is completed. The drawing may be performed while the material is heated.

In FIG. 4C and FIG. 4E, the both ends of the tube material 20 are simultaneously drawn, but the present invention is not limited thereto. It is possible to draw one end and then to draw the other end. In addition, only one end of the both ends of the tube material 20 may be drawn (In a word, it is enough that at least one of the both ends of the tube material 20 is drawn). When only the one end is drawn, it is better that the side, which is not drawn, of the tube material may be held. In this case, for example, the holding may be performed by inserting a core material from the other end side.

In the fabrication of the balloon tube 10, it is desirable to satisfy the formula (1) described below (see FIG. 2 and FIG. 4B).

$$(Lb1/La1)<(Lb2/La2)<(Lb3/La3)$$ Formula (1)

wherein

La1: the shortest distance between the first parts P1 and P1 in the tube material 20;

La2: a full length of one of the first parts P1 and P1 in the axial direction X of the tube material 20;

La3: the shortest distance from one end of the tube material 20 to the first part P1;

Lb1: a full length of the highest drawability part 11 in the axial direction of the balloon tube 10 after the second drawing step;

Lb2: the shortest distance from one end of the bag part 14 to the highest drawability part 11 in the axial direction of the balloon tube 10 after the second drawing step; and Lb3: a full length of the sleeve 13 adjacent to one side of the bag part 14 after the second drawing step.

When (Lb1/La1), (Lb2/La2), and (Lb3/La3) are set so as to satisfy the range defined by the formula (1), in a film thickness T1 of the highest drawability part 11 in the balloon tube 10, a film thickness T2 of the side end part 12, and a film thickness T3 of the sleeve 13, the film thickness T1 of the highest drawability part 11 is the thickest; whereas, the film thickness T3 of the sleeve 13 is the thinnest (the film thickness T2 of the sleeve 13 is a thickness between the film thickness T1 and the film thickness T3). Then, the balloon tube 10, which is preferable for blow-molding as described above, is completed.

Specific examples of the numerical values of (Lb1/La1), (Lb2/La2), and (Lb3/La3) may include numerical values described below:

1.0≤(Lb1/La1)≤1.1
1.2≤(Lb2/La2)≤1.4
1.5≤(Lb3/La3)≤1.9

An example of a fabrication method of a balloon tube having the highest drawability part which is subjected to a chemical processing or which has cuts is briefly explained.

First, the tube material 20 described above is prepared. Then, two part which are separated from each other on the middle part of the tube material 20 are heated. Next, for example, the both ends of the tube material 20 are drawn to produce a tube material having a bag part and sleeves adjacent to the bag part.

After that, a part separated from the both ends of the bag part, which will become the highest drawability part, is subjected to a desired chemical processing, or cuts are formed into the part, thereby obtaining the balloon tube of the present invention. It is better to adopt, for example, the chemical processing or the cutting method described above.

EXAMPLES

The present invention will be explained in more detail based on Examples below.

Production Example

Using a polyamide elastomer (manufactured by Arkema Inc., a glass transition temperature: 25° C.), the elastomer was extrusion molded into a tube having an outer diameter of 1.3 mm and an inner diameter of 0.7 mm in a case of fabricating a balloon, described below, having an outer diameter φ of 4 mm, or the elastomer was extrusion molded into a tube having an outer diameter of 1.6 mm and an inner diameter of 1.0 mm in a case of fabricating a balloon having an outer diameter φ of 6 mm, thereby obtaining a tube material.

Examples 1 and 2

<Fabrication of Balloon Tube>

Using the tube material from Production Example, a balloon tube was fabricated in accordance with the method shown in FIG. 4. Parts La1, La2, and La3 of the tube material correspond to those of the tube material described in FIG. 4B, and the lengths thereof are as shown in Table 1.

First, whole circumferences of two first parts, which were two parts separated from each other on the tube material (the length thereof is La2, the part shown by the sign P1 in FIG. 4B), were heated by heaters (70° C., 30 seconds) (a first heating step).

Then, both ends of the tube material were drawn while they were heated to form a part which will become the highest drawability part between the first parts (the sign 21 in FIG. 4C) (a first drawing step).

Next, whole circumferences of two parts which were on the end sides from the first parts (P1) heated in the first heating step, i.e., two parts which were separated from each other so that all of the heated position of the first parts were sandwiched between them (the sign P2 in FIG. 4D) were heated by heaters (170° C., 30 seconds) (a second heating step).

After that, the both ends of the tube material were drawn while the material was heated, whereby a bag part (the sign 14 in FIG. 4E), in which the highest drawability part (the sign 11 in FIG. 4E) was disposed between the second parts, was formed, and at the same time sleeve (the sign 13 in FIG. 4E) were formed (a second drawing step).

<Fabrication of Balloon>

Using the balloon tube of Example 1 or 2, a balloon having an outer diameter (an outer diameter of the part shown by the sign 31 in FIG. 3E) and a full length (a full length in the axial direction of the parts shown by the signs 31 to 33 in FIG. 3E), which are shown in Table 1, was fabricated by blow-molding in accordance with the method shown in FIG. 3. The blow-molding conditions follow a usual manner.

The balloon, which was obtained by blow-molding the balloon tube of Example 1 or 2, had a uniform film thickness. The balloon tube of the present invention, accordingly, is preferable for stably fabricating a balloon having a uniform film thickness.

TABLE 1

| | Tube material | | | | | | | | | | | Balloon | |
|---|---|---|---|---|---|---|---|---|---|---|---|---|---|
| | Outer | Inner | | | | Balloon tube | | | | | | Outer | Full |
| | diameter [mm] | diameter [mm] | La1 [mm] | La2 [mm] | La3 [mm] | Lb1 [mm] | Lb2 [mm] | Lb3 [mm] | Lb1/La1 | Lb2/La2 | Lb3/La3 | diameter [mm] | length [mm] |
| Example 1 | 1.3 | 0.7 | 2 | 3 | 80 | 2 | 4 | 150 | 1.0 | 1.3 | 1.9 | 4 | 20 |
| Example 2 | 1.6 | 1.0 | 2 | 3.5 | 80 | 2 | 5 | 150 | 1.0 | 1.4 | 1.9 | 6 | 25 |

REFERENCE SIGNS LIST 10, 60 Balloon tube
11, 61 Highest drawability part
12, 62 Side end part
13, 63 Sleeve
14, 64 Bag part
20 Tube material
P1 First part
P2 Second part
25 Heater
30 Balloon
31 Body part
32 Taper part
40 Capillary part
40 Balloon catheter
41 Catheter shaft
42 Hub
50 Metal mold [mold]
51 Cavity
54 Clip

The invention claimed is:

1. A method of fabricating a balloon, comprising:
a first heating step in which two first parts which are separated from each other in an axial direction of a tube material, which is a base of a balloon tube, are simultaneously heated;
a first drawing step in which at least one end of the tube material is drawn to form the highest drawability part at which the drawability is the highest between the two first parts;
a second heating step in which, in the tube material, two second parts, which are separated from each other so that all of the plurality of the heated positions of the first parts are sandwiched between them, are simultaneously heated;
a second drawing step in which at least one end of the tube material is drawn to form a bag part having the highest drawability part disposed between the two second parts, and
mounting, on a mold, the balloon tube obtained upon completion of the second drawing step, and performing blow-molding on the balloon tube.

2. The method of fabricating a balloon according to claim 1, wherein in the second drawing step, sleeves are formed adjacent to both sides of the bag part.

3. The method of fabricating a balloon according to claim 2, which satisfies the following formula (1):

$(Lb1/La1) < (Lb1/La2) < (Lb3/La3)$  Formula (1)

wherein
La1: the shortest distance between the first parts in the tube material before the first heating step;
La2: a full length of one of the first parts in the axial direction of the tube material before the first heating step;
La3: the shortest distance from one end of the tube material to the first part;
Lb1: a full length of the highest drawability part in the axial direction of the balloon tube after the second drawing step;
Lb2: the shortest distance from one end of the bag part to the highest drawability part in the axial direction of the balloon tube after the second drawing step; and
Lb3: a full length of the sleeve adjacent to one side of the bag part after the second drawing step.

4. A method of fabricating a balloon, comprising:
a first heating step in which two first parts which are separated from each other in an axial direction of a tube material, which is a base of a balloon tube;
a first drawing step in which at least one end of the tube material is drawn to form the highest drawability part at which the drawability is the highest between the two first parts;
a second heating step in which, in the tube material, two second parts, which are separated from each other so that all of the plurality of the heated positions of the first parts are sandwiched between them, are heated;
a second drawing step in which at least one end of the tube material is drawn to form a bag part having the highest drawability part disposed between the two second parts, and
mounting, on a mold, the balloon tube obtained upon completion of the second drawing step, and performing blow-molding on the balloon tube, wherein
in the second drawing step, sleeves are formed adjacent to both sides of the bag part, and the method satisfies the following formula (1):

$(Lb1/La1) < (Lb2/La2) < (Lb3/La3)$  Formula (1)

wherein
La1: the shortest distance between the first parts in the tube material before the first heating step;
La2: a full length of one of the first parts in the axial direction of the tube material before the first heating step;
La3: the shortest distance from one end of the tube material to the first part;
Lb1: a full length of the highest drawability part in the axial direction of the balloon tube after the second drawing step;
Lb2: the shortest distance from one end of the bag part to the highest drawability part in the axial direction of the balloon tube after the second drawing step; and
Lb3: a full length of the sleeve adjacent to one side of the bag part after the second drawing step.

* * * * *